US006998393B2

(12) United States Patent  (10) Patent No.: US 6,998,393 B2
Jin et al.  (45) Date of Patent: Feb. 14, 2006

(54) AQUESPHERES, THEIR PREPARATION AND USES THEREOF

(75) Inventors: Tuo Jin, Highland Park, NJ (US); Hua Zhu, Palinboro, NJ (US); Jiahao Zhu, Brooklyn, NY (US)

(73) Assignee: Biopharm Solutions, Inc., Highland Park, NJ (US)

( * ) Notice: Subject to any disclaimer, the term of this patent is extended or adjusted under 35 U.S.C. 154(b) by 86 days.

(21) Appl. No.: 10/291,327

(22) Filed: Nov. 8, 2002

(65) Prior Publication Data

US 2003/0059402 A1    Mar. 27, 2003

Related U.S. Application Data

(63) Continuation-in-part of application No. 09/886,555, filed on Jun. 21, 2001, now Pat. No. 6,805,879.

(60) Provisional application No. 60/384,971, filed on Jun. 3, 2002, provisional application No. 60/418,100, filed on Oct. 11, 2002, provisional application No. 60/214,037, filed on Jun. 23, 2000.

(51) Int. Cl.
*A61K 9/62*    (2006.01)

(52) U.S. Cl. .............................. 514/57; 514/59; 536/45; 424/489; 424/490

(58) Field of Classification Search ................ 514/57, 514/59; 436/45; 536/1.11, 55.1; 424/489, 424/490
See application file for complete search history.

(56) References Cited

U.S. PATENT DOCUMENTS 5,716,644 A    2/1998   Zale et al.

FOREIGN PATENT DOCUMENTS

WO          9640071      10/1996

OTHER PUBLICATIONS

Cleland, J. L. et al, "Stable Formulations of Recombinant Human Growth Harmone and Interferon-gamma for Microencapsulation in Biodegradable Microspheres", Pharmaceutical Research, 1996, 13(10), 1465-1475.*
A. Berthold et al "Preparation and characterization of chitosan microspheres as drug carrier for prednisolone sodium phosphate as model antiinflammatory drugs". Journal of Controlled Release, 1996, 39, 17-25.*
U.S. Appl. No. 09/886,555, Jin, Tuo, Li Chen, and Hua Zhu, for Stable Polymer Aqueous/Aqueous Emulsion Sylstem and Uses Thereof (2001). [Exhibit 3].
Langer, R., Folkman, J., "Polymers for the sustained release of proteins and other macromolecules," Nature 263, 797-800 (1976). [Exhibit 4].

CAS, Results of search on chemical abstracts on the subject of sustained release of proteins based on degradable polymers. (2002). [Exhibit 5].
Weert, M. v., Hennink, W. E., Jiskoot, W., "Protein instability in poly(lactic-co-glycolic acid) microprarticles," Pharm. Res. 17, 1159-1167 (2000). [Exhibit 6].
Bartus, R. T., Tracy, M.A., Emerich, D.F., Zale, S.E., "Sustained delivery of proteins for novel therapeutic products," Science 281, 1161-1162 (1998). [Exhibit 7].
Burke, P. A., "Controlled release protein therapeutics: effects of process and formulation on stability," Handbook of pharmaceutical controlled release technology, Marcel Dekker, 661-692 (2000). [Exhibit 8].
Cleland, J. L., Jones J.S., "Stable formulations of recombinant human growth hormone and interferon-γ for microencapsulation in biodegradable mircospheres," Pharm. Res. 13, 1464-1475 (1996). [Exhibit 9].
Johnson, O. L., "The stabilization and encapsulation of human growth hormone into biodegradable microspheres," Pharmaceutical Research 14, 730-735 (1997). [Exhibit 10].
Cunningham, B. C., Mulkerrin, M. G., Wells, J. A., "Dimerization of human growth hormone by zinc," Science 253, 545-548 (1991). [Exhibit 11].
Sanchez, A., Villamayor, B., Guo, Y., McIver, J., Alonso, M. J., "Formulation strategies for the stabilization of tetanus toxoid in poly(lactide-co-glycolide) microspheres," Intern. J. Pharm. 185, 255-266 (1999). [Exhibit 12].
Schwendeman, S. P., Tobio, M., Jaworowicz, M., Alonso, M. J., Langer, R., "New strategies for the microencapsulation of tetanus vaccine," J. Microencapsulation 15, 299-318 (1998). [Exhibit 13].

(Continued)

*Primary Examiner*—James O. Wilson
*Assistant Examiner*—Ganapathy Krishnan
(74) *Attorney, Agent, or Firm*—Law Offices of Albert Wai-Kit Chan, LLC

(57)    ABSTRACT

This invention provides method for sustained release delivery of structurally delicate agents such as proteins and peptides. Using a unique emulsion system (Stable polymer aqueous-aqueous emulsion), proteins and peptides can be microencapsulated in polysacchride glassy particles under a condition free of any chemical or physical hazard such as organic solvents, strong interfacial tension, strong shears, elevated temperature, large amount of surfactants, and cross-linking agents. Proteins loaded in these glassy particles showed strong resistance to organic solvents, prolonged activity in hydrated state, and an excellent sustained release profile with minimal burst and incomplete release when being further loaded in degradable polymer microspheres. This invention provides a simple yet effective approach to address all the technical challenges raised in sustained release delivery of proteins.

19 Claims, 11 Drawing Sheets

OTHER PUBLICATIONS

Morlock, M., Koll, H., Winter, G., Kissel, T., "Microencapsulation of rh-erythropoietin, using biodegradable poly(D,L-lactide-co-glycolide):protein stability and the effects of stabilizing excipients," European Journal of Pharmaceutics and Biopharmaceutics 43, 29-36 (1997). [Exhibit 14].

Yoshioka, S., Aso, Y., Kojima, S., "Dependence of the molecular mobility and protein stabilitiy of freeze-dried γ-globulin formulations on the molecular weight of dextran," Pharmaceutical Research 14, 736-741 (1997). [Exhibit 15].

Weert, M. v. d., Hof, R. v., Weerd, J. v. d., Heeren, M.A., Posthuma, G., Hennink, W. E., Crommelin D. J. A., "Lysozyme distribution and conformation in a biodegradable polymer matrix as determined by FTIR techniques," J. Controlled Release 68, 31-40 (2000). [Exhibit 16].

Morita, T., Horikiri, Y., Suzuki, T., Yoshino, H., "Preparation of gelatin microparticles by co-lyophilization with poly (ethylene glycol): characterization and application to entrapment into biodegradable microspheres," International Journal of Pharmaceutics 219, 127-137 (2001). [Exhibit 17].

Maa, Y.-F., Nguyen, P-A., Hsu, S. W., "Spray-drying of air-liquid interface sensitive recombinant human growth hormone," J. Pharm. Sci., 87, 152-159 (1998). [Exhibit 18].

Morita, T., Horikiri, Y., Yamahara, H., Suzuki, T., Yoshino, H., "Formation and isolation of spherical fine protein microparticles through lyophilization of protein-poly (ethylene glycol) aqueous mixture," Pharm. Res. 17, 1367-1373 (2000). [Exhibit 19].

Park, T. G., Lee, H.Y., Nam, Y.S., "A new preparation method for protein loaded poly(D,L-lactic-co-glycolic acid) microspheres and protein release mechanism study," J. Controlled Release 55, 181-191 (1998). [Exhibit 20].

Franssen, O., Hennink, W. E., "A novel preparation method for polymeric microparticles without the use of organic solvents," Intern. J. Pharm., 168, 1-7 (1998). [Exhibit 21].

Schwendeman, S. P., Cardamone, M., Brandon, M. R., Klibanov, A., Langer, R., "Stability of proteins and their delivery from biodegradable polymer microspheres," S. C. H. Bernstein, Ed., *Microparticulate Systems for the Delivery of Proteins and Vaccines,* (Mercel Dekker, New York, 1996), vol. 77. [Exhibit 22].

Liu, W. R., Langer, R., Klibanov, A. M., "Moisture-induced aggregation of lyophilized proteins in the solid state," Biotech. Bioeng. 37, 177-184 (1991). [Exhibit 23].

Bittner, B., Morlock, M., Koll, H., Winter, G., Kissel, T., "Recombinant human erythropoietin (rhEPO) loaded poly (lactide-co-glycolide) microspheres: influence of the encapsulation technique and polymer purity on microsphere characteristics," Eur. J. Pharm. Biopharm. 45, 295-305 (1998). [Exhibit 24].

Takahata, H., Lavelle, E.C., Coombes, A.G.A., Davis, S.S., "The distribution of protein associated with poly(DL-lactide co-glycolide) microparticles and its degradation in simulated body fluids," J. Controlled Release 50, 237-246 (1998). [Exhibit 25].

* cited by examiner

2A

2B

3A

3B

AQUESPHERES, THEIR PREPARATION AND USES THEREOF

This application claims priority of U.S. Ser. No. 60/214,037, filed Jun. 23, 2000; is a continuation-in-part of U.S. Ser. No. 09/886,555, filed Jun. 21, 2001, now U.S. Pat. No. 6,805,879, issued Oct. 19, 2004, claiming benefit of U.S. Ser. No. 60/214,037, filed Jun. 23, 2000; Int'l App'l No. PCT/CN01/01033, filed Jun. 22, 2001, claiming benefit of U.S. Ser. No. 60/214,037, filed Jun. 23, 2000; U.S. Ser. No. 60/384,971, filed Jun. 3, 2002; and U.S. Ser. No. 60/418,100, filed Oct. 11, 2002, the contents of which are incorporated by reference here into this application.

Throughout this application, various references are referred to. Disclosures of these publications in their entireties are hereby incorporated by reference into this application to more fully describe the state of the art to which this invention pertains.

FIELD OF THE INVENTION

The present invention demonstrates a novel method for preparing a novel particulate glassy system which effectively preserve structure/activity of proteins peptides, DNA, liposomes and live viruses during formulation process, storage, and application.

BACKGROUND OF THE INVENTION

Due to the impermeability and short half-life, most of protein therapeutics require frequent injection. To reduce injection frequency, development of sustained release dosage forms has been a long-standing research focus since 1970s (1). In spite of extensive research efforts (2), up to now, sustained release formulation technology has succeeded in only one protein drug, recombinant human growth hormone (rhGH). The major roadblocks are invariably the protein instability in formulation process and at the site of release (3, 4) as well initial burst and incomplete release. Various strategies to improve protein stability in microencapasulation have been reported in last decades (3, 5, 6). Many of these approaches, however, only address one or some issues, leaving others unsolved or even creating new problems. Some methods are feasible for only specific proteins, and some reports are contradictory to each other due to different focal points of researchers. For example, for the only commercially available long-acting protein, sustained release rhGH, the protein was stabilized by forming complex with zinc ions (7) based on that natural hGH forms complex with zinc in secretory granules (8). When zinc was co-encapsulated with another protein, erythropoietin (EPO) for example, up to 40% of released proteins was aggregated (9), which could result in unwanted immunogenisity. In order to protect proteins from organic solvents used in microencapsulation, sugars, inorganic salts or other conceivable excipients are used to preformulate proteins into solid particles prior to microencapsulating them into degradable polymer microspheres through a solid-in-oil-water (S-O-W) emulsification process (7, 9, 10). These excipients often resulted in considerable burst release due to strong osmotic pressure created by their high solubility (11) and rapid dissolution (12). When highly soluble ammonium sulfate was used to stabilize EPO in microencapsulation, burst release accounted up to 55% of total drug (9).

Cleland and Jones studied the effects of various excipients on protection of rhGH and interferon γ (IFN-γ) in water-in-oil-in-water (W-O-W) and S-O-W encapsulation processes, and found that mannitol or trehalose were the best in preventing proteins from aggregation during microencapsulation process were prevented (6). Sanchez et al. examined the protection effects of similar excipients for another protein, tetanus toxoid, and found dextran, that was ineffective for recovering rhGH and IFN-γ in Cleland and Jones report, showed best protection for the protein (based on ELISA) at the release phase under a hydrated condition (10). It seems that small sugars offer better protection in dehydration steps (drying), while polysacchrides are more effective in a hydrated step (release) (13). A burst release of 60% of total loading was observed from dextran included PLGA microspheres prepared by Sanchez et al. This burst release may be attributed to the particle size of the co-lyophilized protein-excipient particles (14, 15).

The size of pre-formed protein particles plays an important role in a S-O-W process. Morita et al. demonstrated that when the mean diameter of solid protein particles increased from 5 to 20 μm, the initial release almost doubled, and encapsulation efficiency dropped from 80% to 20% (15). Cleland et al. discussed different approaches for reducing protein particle size for a S-O-W process (6). Homogenizing a lyophilized protein-excipients powder in organic solvents can only result particles above 10 □m in diameter, while milling the powders to smaller size may cause protein denature due to the shears and heat generated (6). Spray drying may produce protein particles to desired size, but shear and heat at atomization as well as the presence of air-liquid interface may cause denaturation (6, 16). Moreover, surfactants must be used in spray drying and spray freeze-drying that facilitate contact and interaction between proteins and dichloromethane (the solvent most frequently used in microencapsulation) (6). Maa et al. reported that complexation of rhGH with zinc prior to spray drying can effectively prevent aggregation of the protein (16). Again, zinc complexation can denatrue proteins other than rhGH (9). Morita et al. prepared fine protein particles by a freezing-induced precipitation with a co-solution of proteins and PEG (15, 17). But the protein particles still have to be exposed to organic solvents directly during microencapsulation. Direct contact of unprotected proteins with PLGA will cause incomplete release by strong adsorption of the proteins on the internal surface of the polymer matrix (18). To avoid the hydrophilic-hydrophobic interface, aqueous two-phase systems were used for preparing polysaccharide particles (19, 20). However, the dispersed phases need to be stabilized by covalent or ionic cross-linking, another potential cause for protein denaturation.

For sustained release of delicate proteins, an approach that can address all these important issues is highly desired. Due to the long-standing difficulties discussed above, it is unlikely that this task can be accomplished with the existing approaches. Microencapsulation strategies based on new scientific concepts are required.

In one of our previous patent application, we have reported (as the first time according to best of our knowledge) a unique microencapsulation system, stable polymer aqueous-aqueous emulsion (24). This system differs from conventional emulsions in that both the dispersed and continuous phases are aqueous. The system is also different from so-called polymer aqueous two-phase systems that form two block phases in absence of continuous mixing. This emulsion is stable for up a week without any (covalent or ionic) cross-linking treatment. Due to these unique characteristics, delicate therapeutics such as proteins, liposomes or live viruses can be loaded into the droplets of this emulsion under a condition free of chemical or physical hazards such as organic solvents, concentrated salts, extreme pH, crosslink agents, high shear stress, high interfacial tension and high temperature. By freeze-drying or other drying methods, dispersed phase of the emulsion can form glassy particles of defined shape and uniform size for various delivery purposes (inhalation or sustained release). Our previous work has established the proof-of-principle that all the stability problems raised in protein microencapsulation, such as the processes of protein loading, drying, storage and release (3), can be addressed using this unique system. In addition, all the ingredients used are those proven for injection into human.

This present application further demonstrates applications of this stable aqueous-aqueous emulsion system in delivery of protein drugs. Proteins can be loaded into the dispersed phase of the aqueous-aqueous emulsion system and form glassy particles by freeze-drying thereafter. The entire preparation process is free of any chemical physical hazards. Protein activity can be well preserved during this preparation process. Proteins loaded in the glassy particles made via the emulsion system (called AqueSphere(s) hereafter) showed strong resistance to organic solvents, prolonged activity in hydrated state at 37° C., as well as linear release profile with minimal burst and incomplete release when being further loaded in degradable polymer microsphere.

SUMMARY OF THE INVENTION

It is an object of this invention to provide a method to prepare polymeric microspheres for sustained release of protein therapeutics. The method is an application of material system, stable polymer aqueous-aqueous emulsion and AqueSphres (polysaccharide glassy particles made by solidification of the emulsion system), which were described in our earlier patent application (24). The method comprises 1) loading proteins in the droplets of the stable aqueous-aqueous emulsion system; 2) preparation of AqueSpheres with diameter ranging between 1–5 microns for inhalation protein delivery; 3) encapsulation of AqueSpheres into PLGA and other degradable polymer microspheres and injectable implants; 4) preparation of AqueSpheres loaded with structurally delicate substances other than proteins (such as liposomes and live viruses) for inhalation, nasal spray and other therapeutic uses.

A major difficulty that delayed development of sustained release or non-invasive protein formulations is that proteins are denatured during the formulation process. To prevent protein denature, a formulation process must be free of (or proteins must be protected from) the chemical physical hazards discussed above. In achieving this objective, however, properties and functions of the final product such as particle size and shape, release profile, loading efficiency, prolonged activity at the site of release and so forth should not be compromised. It is also preferred that the manufacture process can be easy, reproducible and environmentally friendly.

The present invention has demonstrated a simple solution for all these objectives above.

First, fragile biological agents such as proteins can be loaded into the dispersed phase of the stable polymer aqueous-aqueous emulsion system (24) under a condition free of any chemical or physical hazard. A uniform size distribution of the droplets can be achieved by a conventional emulsification process under appropriate shear stress and low interfacial tension (due to the aqueous-aqueous nature). Then the system can be freeze-dried to dry powder in which the polymer droplets converted to glassy particles of uniform sizes (1–5 um in diameter). Once the glassy particles are formed, the structure of the loaded are preserved and protected. Due to its hydrophilicity and high glassy transition temperature, the system offers strong resistance to organic solvents as well as resistance to ambient temperature and moisture (in terms of protein activity retention). The bio-agents-loaded AqueSpheres can therefore be used for inhalation drug delivery (based on their size range) or subjected to further formulation process with biodegradable hydrophobic polymers for sustained release.

For preparation of sustained release microspheres, AqueSpheres can be loaded into PLGA (or other degradable polymers) microspheres by conventional solid-in-oil-in-water (S-O-W) or solid-in-oil-in-oil (S-O-O) emulsification methods. A recovery experiment from PLGA microspheres indicated that the AqueSpheres remain intact inside of the microspheres (Example 4).

Bioactivity of the proteins loaded in AqueSpheres was retained after contacted with organic solvents and after microencapsulation process as assayed in cell proliferation (Example 5, 6, and 7), indicating that conformation of proteins were well protected in the glassy matrix of polysaccharide. In addition, the activity retention of proteins after miroencapsuleted in PLGA microspheres (Example 7) suggests high encapsulation efficiency.

The most challenging task in developing sustained release protein dosage forms is to ensure protein activity in a hydrated state at physiological temperature (21). Hydration and temperature elevation will increase the mobility of proteins and lower the energy barrier for protein hydrolysis, aggregation and conformation change. With the present technology, proteins loaded in AqueSpheres showed prolonged activity in a hydrated state at 37° C. (Example 8). Recombinant human erythropoietin (rhEPO) which has in vivo half life of 8.5 hrs and in vitro half life of a day showed a half life of a week under a hydrated condition when loaded in AqueSpheres (Example 8). The AqueSphere matrix formed a viscous phase surrounding the proteins so that limited protein mobility and the chance for proteins to contact with each other and other species (the degradable polymer and enzymes).

Burst effect, defined as rapid release of considerable amount of loadings in the initial period of administration, is another common problem in developing sustained release dosage forms of protein drugs. Burst effect is found for both injectable implants and microsphere formulations, although the causes may be different. Accompanying with burst effect is incomplete release that part of the proteins loaded strongly interact with the polymer matrix and are not able to release in the required period. Having proteins pre-encapsulated in AqueSpheres prior to loading into degradable polymers can effectively prevent burst effect, and at the same time, reduce the portion of incomplete release (Example 9).

Moreover, AqueSpheres helps to reduce local acidity generated by polymer degradation. Local acidity is another cause believed for protein denaturation during release period. AqueSpheres form inter-connected channels when being hydrated in degradable polymer matrix that their viscous nature limits diffusion of macromolecular proteins but permeable to small molecular buffers. This nature allow the local acidity be buffered in the sustained release process. In addition, the surface modifier (sodium alginate) itself possesses significant buffer effect.

This invention provides a simple yet effective solution for all the long-standing technical difficulties in developing sustained release protein microspheres (3–5).

Figure 1:
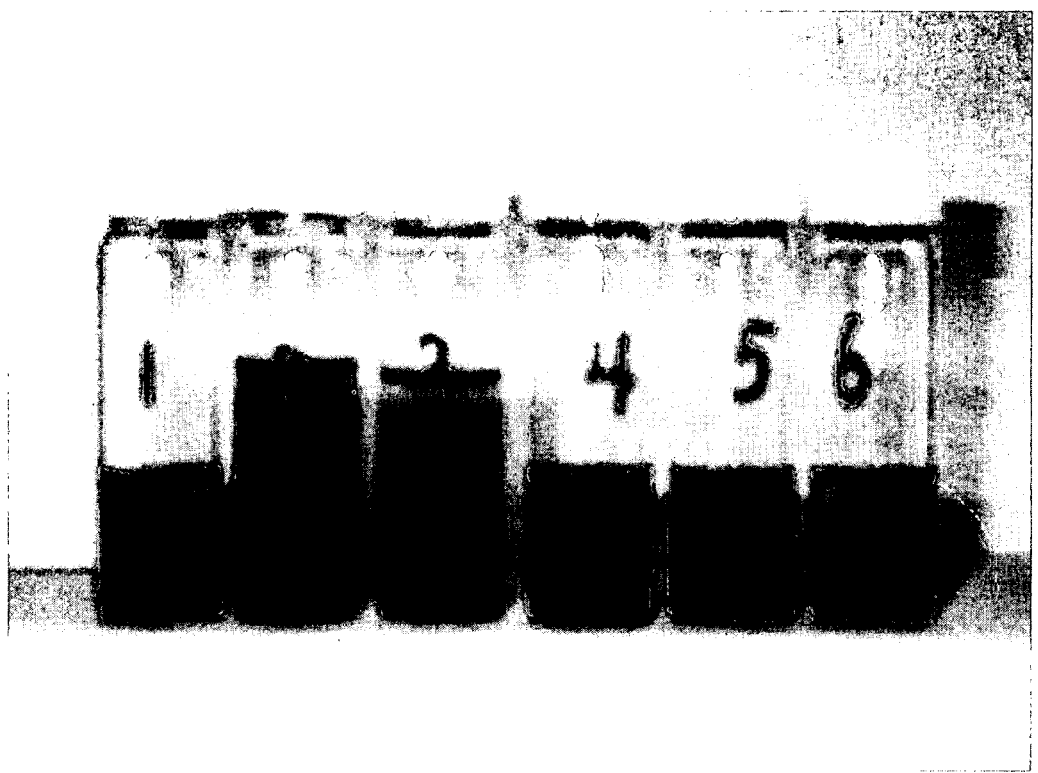
FIG. 1. Stable polymer aqueous-aqueous emulsion loaded with myoglobin in the dispersed phase. The picture was taken one week after the samples were prepared.

(1) Dispersed phase: 1 ml, containing 5 w/w % myoglobin and 20 w/w % dextran; Continuous phase: 5 ml, containing 1 w/w % sodium alginate and 20 w/w % PEG.

(2) Dispersed phase: 1 ml, containing 5 w/w % myoglobin and 20 w/w % dextran; Continuous phase: 10 ml, containing 1 w/w % sodium alginate and 20 w/w % PEG.

(3) Dispersed phase: 0.5 ml, containing 5 w/w % myoglobin and 20 w/w % dextran; Continuous phase: 10 ml, containing 1 w/w % sodium alginate and 20 w/w % PEG.

(4) Dispersed phase: 1 ml, containing 5 w/w % myoglobin and 20 w/w % dextran; Continuous phase: 5 ml, containing 20 w/w % PEG.

(5) Dispersed phase: 1 ml, containing 5 w/w % myoglobin and 20 w/w % dextran; Continuous phase: 5 ml, containing 1 w/w % sodium alginate, 20 w/w % PEG and 10 mM NaCl.

(6) Dispersed phase: 1 ml, containing 5 w/w % myoglobin and 20 w/w % dextran; Continuous phase: 5 ml, containing 1 w/w % sodium alginate, 20 w/w % PEG and 100 mM NaCl.

The brown dispersed phase (myoglobin/dextran) in samples (4) and (6) started to fuse right after preparation and formed a block phases at the bottom of over night. Those in sample (1), (2), (3) and (5) were unchanged in a week as observed using a microscope.

Figure 2:
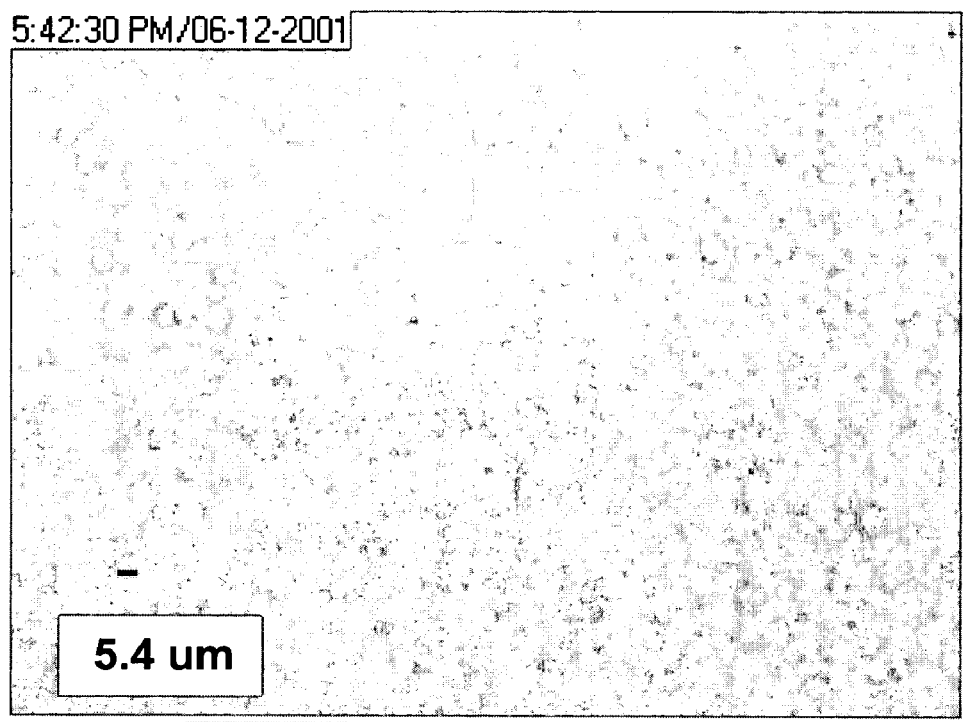
Figure 2:
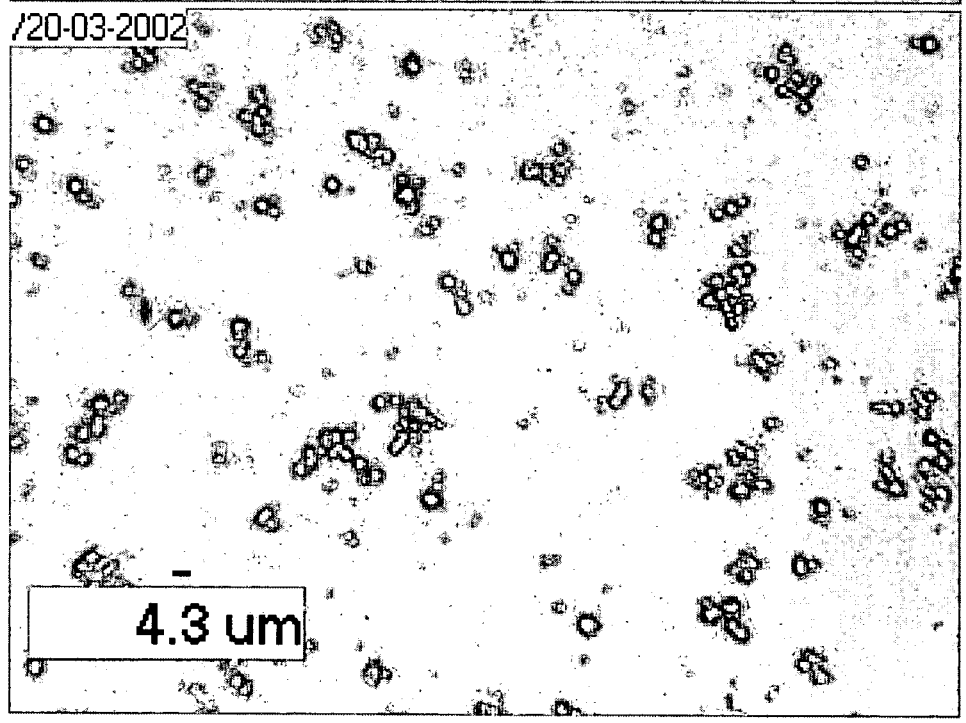

FIG. 2. Microscopic images of stable aqueous-aqueous emulsion and polysacchride particles.

Figure 3:
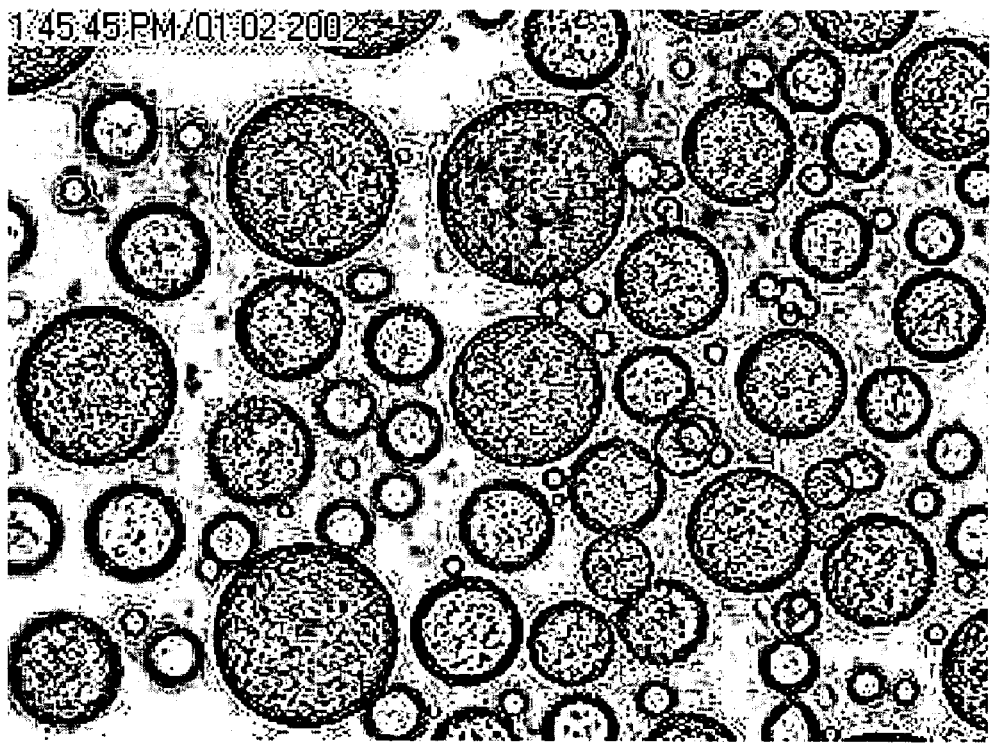
Figure 3:
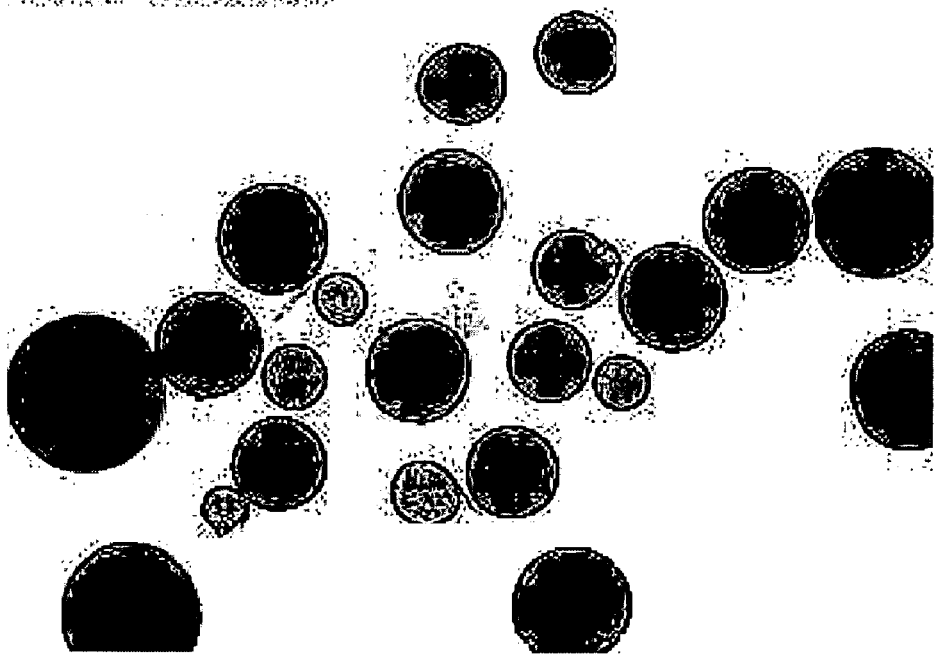

(2A) Microscopic image of the stable aqueous-aqueous emulsion shown in FIGS. 1-1; (2B) microscopic image after (2A) was freeze-dried and washed with dichloromethane (to remove the dried PEG phase FIG. 3. Preparation of PLGA microspheres by a S-O-W double emulsification 3A) Microscopic image of a S-O-W double emulsion for which AqueSpheres are evenly suspended in the organic PLGA phase.

3B) Solidified PLGA microspheres in which AqueSpheres are encapsulated.

Figure 4:
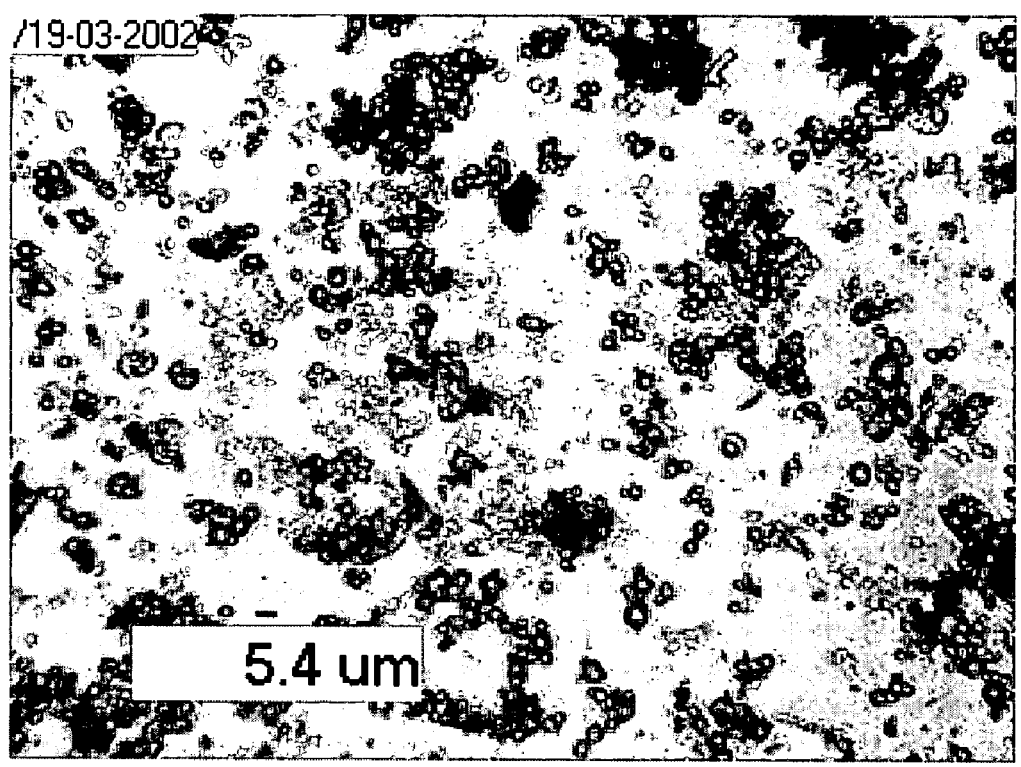

FIG. 4. Microscopic image of AqueSpheres recoved from PLGA microspheres (as shown in FIG. 3B). The size and shape of recovered AqueSpheres are identical to that before encapsulated in PLGA microspheres (FIG. 2B).

Figure 5:
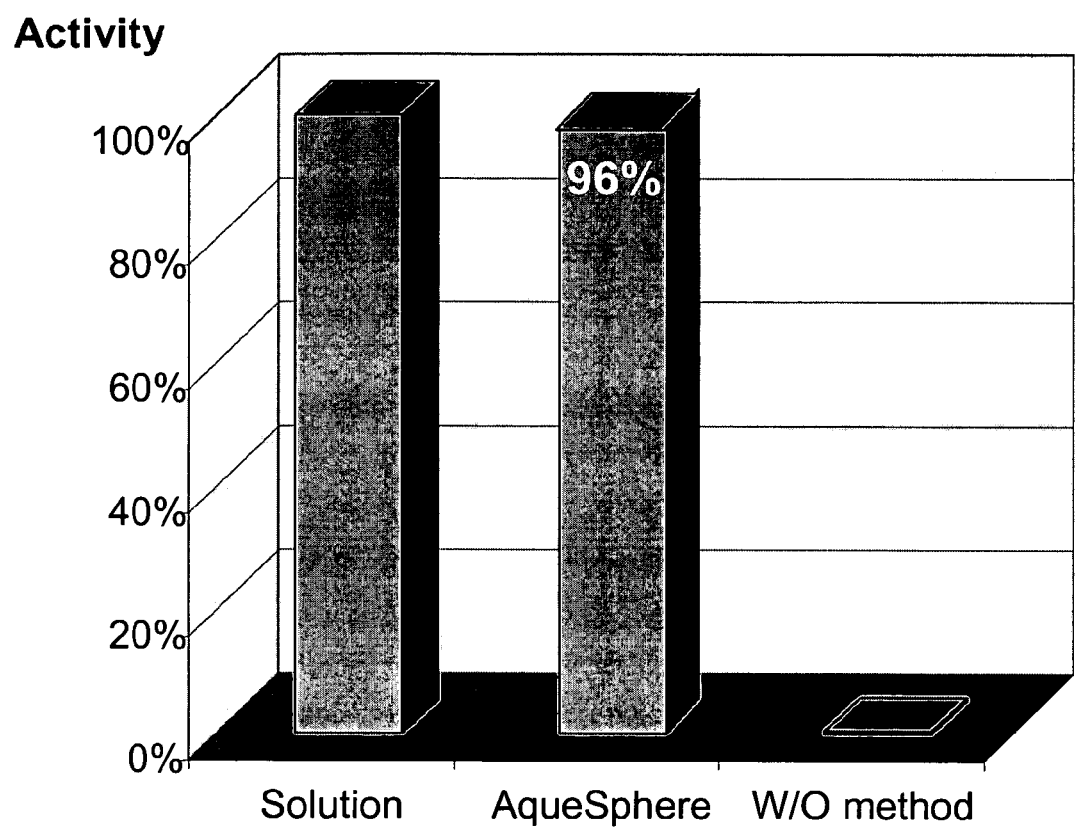

FIG. 5. Catalytic activity of β-galactosidase before and after being encapsulated in AqueSpheres followed by washing with dichloromethane.

Compared with β-galactosidase solution, its activity only slightly reduced after encapsulation in AqueSpheres, followed by washing with organic solvent. While, activity was lost when the protein was loaded in dextran particles through a water-in-oil emulsification method.

Figure 6:
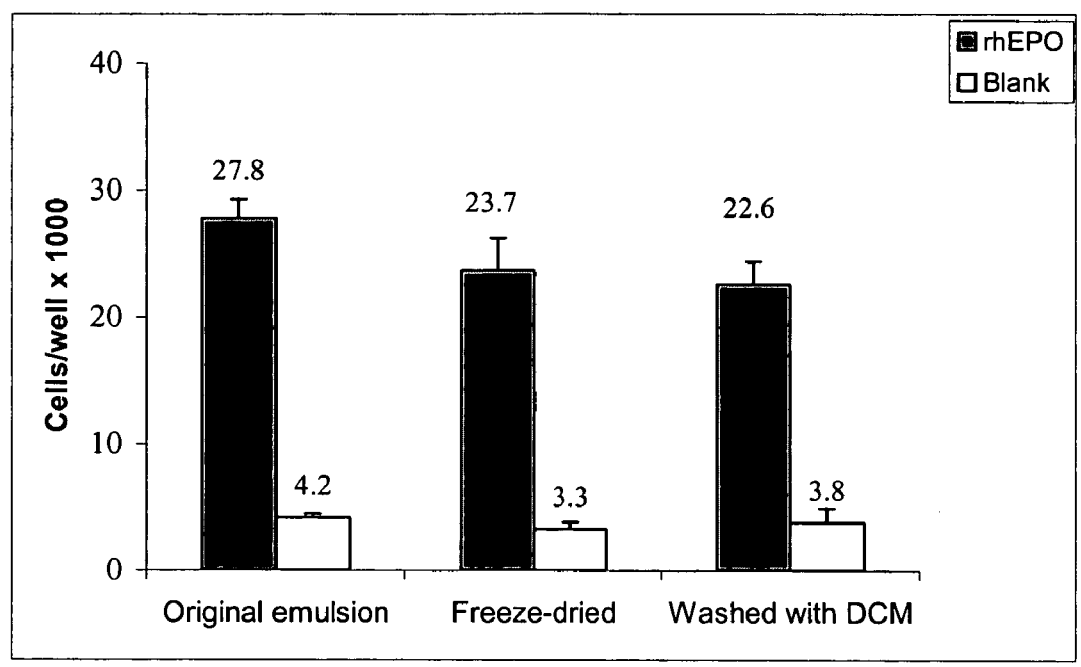

FIG. 6. Bioactivity of rhEPO assayed by proliferation of TF1 cells after each preparation step.

Equivalent amounts of rhEPO were reconsitituted and incubated with TF1 cells after emulsification, freeze-drying, and washing with dichloromethane, respectively. Cells proliferated were counted under a microscope. Numbers of cells per well were averaged from three wells.

Figure 7:
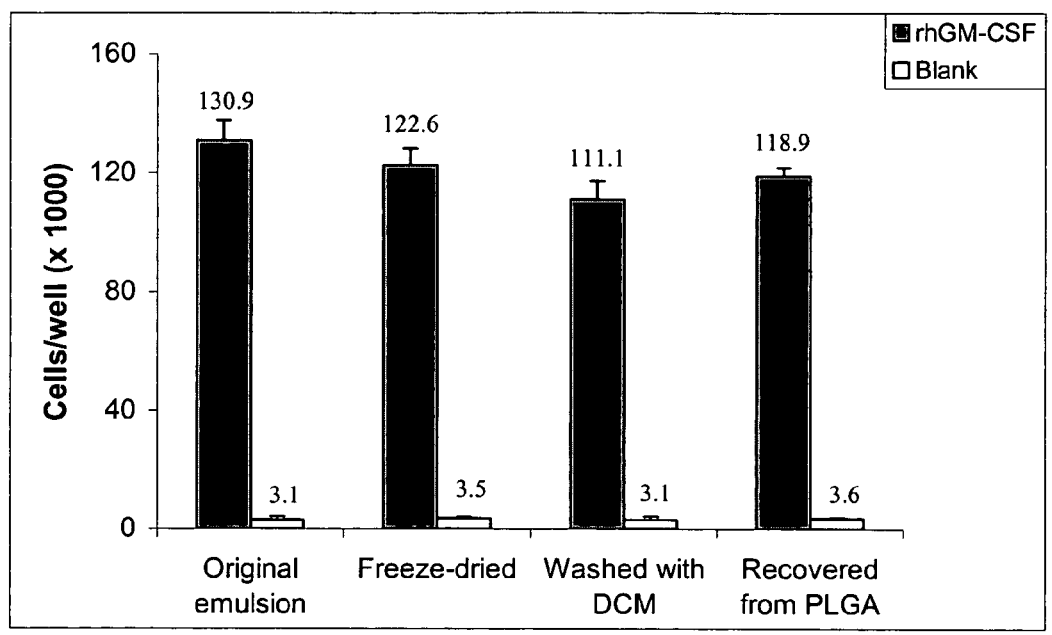

FIG. 7. Bioactivity of rhGM-CSF assayed by proliferation of TF1 cells after each preparation step.

Equivalent amounts of rhGM-CSF were reconsitituted and incubated with TF1 cells after emulsification, freeze-drying, washing with dichloromethane, and recovery from PLGA microspheres in which the protein was encapsulated, respectively. Cells proliferated were counted under a microscope. Numbers of cells per well were averaged from three wells.

Figure 8:
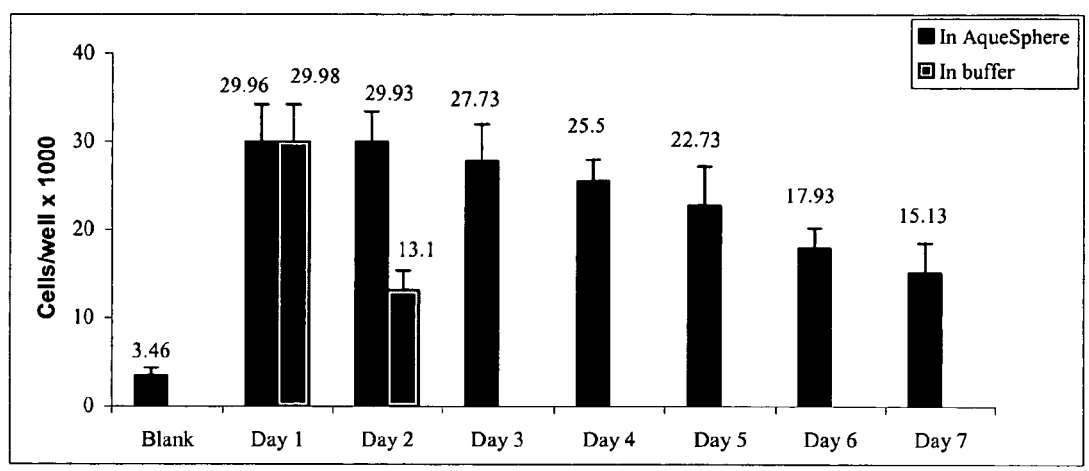

FIG. 8. Bioactivity of rhEPO assayed by proliferation of TF1 cells after incubation in a hydrated form at 37° C.

Activity after incubation in a hydrated state at physiological temperature: The protein loaded in AqueSpheres was added with water twice of their mass and incubated 37° C. for different days prior to cell culture. The activity was indicated by the average number of cells grew in each well. For control, equivalent amount of rhEPO was incubated in a PBS buffer and assayed under identical conditions.

Figure 9:
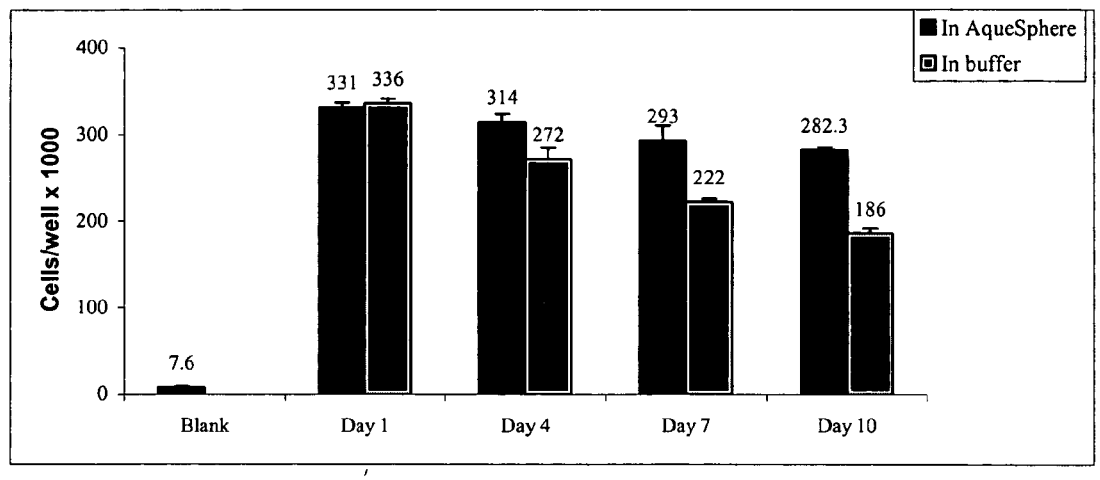

FIG. 9. Bioactivity of rhGM-CSF assayed by proliferation of TF1 cells after incubation in a hydrated form at 37° C.

Activity after incubattion in a hydrated state at physiological temperature: The protein loaded in AqueSpheres was added with water twice of their mass and incubated 37° C. for different days prior to cell culture. The activity was indicated by the average number of cells grew in each well. For control, equivalent amount of rhGM-CSF was incubated in a PBS buffer and assayed under identical conditions.

Figure 10:
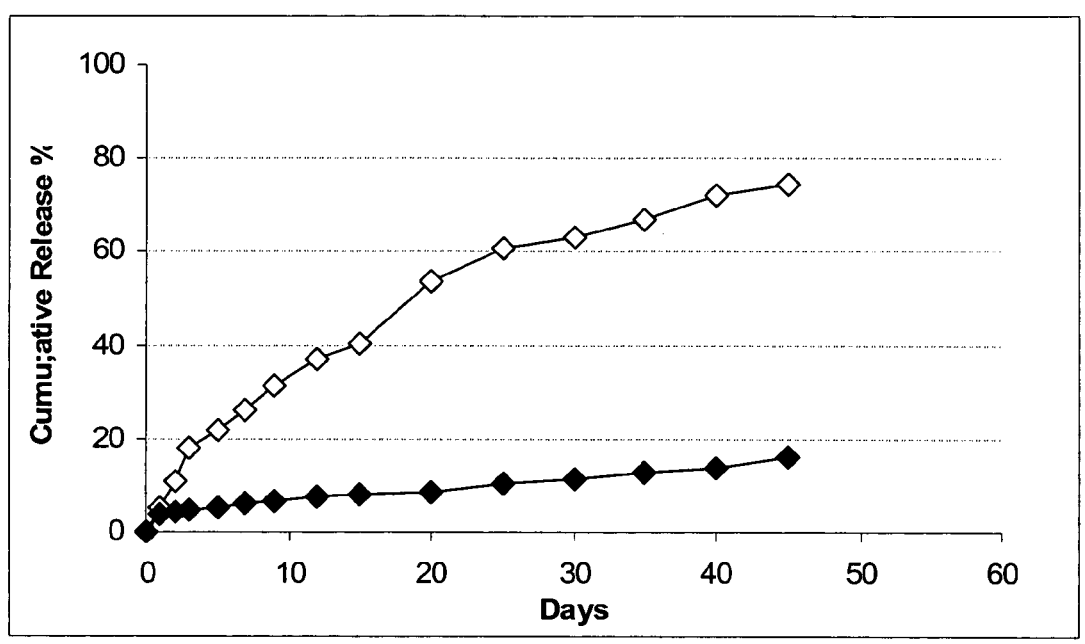

FIG. 10. Release profile of myoglobin from PLGA microspheres. The release study was carried out by suspending 50 mg microspheres in 2 ml of 0.1 M BPS buffer at 37° C. Amount of myoglobin released was assayed using a BCA method. ◆: Pure myoglobin particles directly encapsulated in microspheres made of ester-end PLGA with lactide/glycolide ratio of 50/50 and molecular weight of 6K; ◇: Myoglobin-dextran particles encapsulated in microspheres made of the same PLGA as above.

Figure 11:
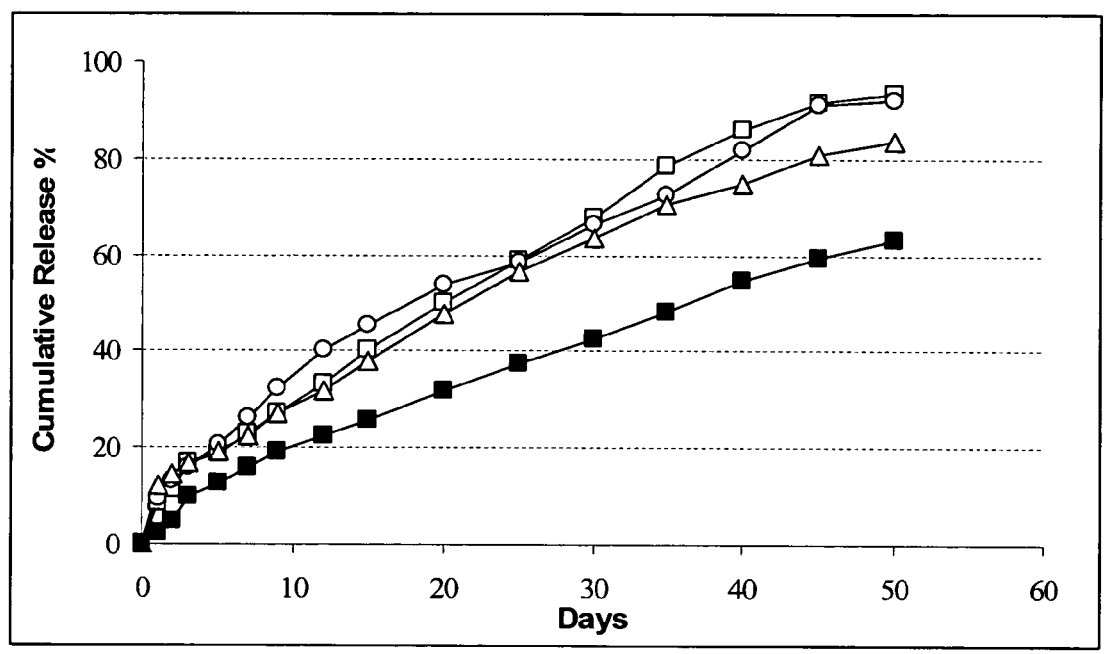

FIG. 11. Release profiles of myoglobin microencapsulated in PLGA microspheres as AqueSpheres.

○: from microspheres of PLGA with lactide/glycolide ratio (L/G) of 50/50 and molecular weight (MW) of 12K; □: from microspheres of PLGA with L/G of 65/35 and MW of 12K; Δ: from microspheres of PLGA with L/G of 75/25 and MW of 12K; ■: from microspheres of PLGA with L/G of 65/35 and MW of 20K.

DETAILED DESCRIPTION OF THE INVENTION

The present invention provides a method to use polymer aqueous-aqueous emulsion system (20) to deliver proteins and other biological agents in a sustained release dosage forms. When biological agents are loaded in a polysaccharide solution, followed by emulsification and freeze-dry, their structure is "fixed" in a hydrophilic glassy matrix. Such glassy particles (AqueSpheres) offer a series advantages that cannot be all achieved by any other reported method.

Small and uniform particle sizes of pre-protected proteins play an important role in control of the burst release and improving encapsulation efficiency in a S-O-W or a S-O-O micronecapsulation process (6, 13). This invention provides a method to prepare protein-loaded polysaccharide glassy particles of defined shape and uniform size (1–3 um, Examples 1 and 2) under a condition free of organic solvents, strong interfacial tension, strong shears, elevated temperature, large amount of surfactants, and cross-linking agents. These factors are known to denature proteins in one or several steps of microencapsulation process (3,6,21). As discussed above, however, no a method known to date (W/O emulsion, spray drying, spray freeze-drying, freeze-drying, milling, and in situ cross-linking) can be used for preparing protein particles without compromising with the hazards above.

In addition, spray drying and spray freeze-drying can only be used to prepare particles with low molecular weight sugars or salts as the protein stabilizers because polysaccharide solutions are too viscous to spray. The present stabilized emulsification method allows viscous aqueous solution be easily micronized. As discussed later, polysaccharide stabilizers possesses a number of advantages for both protein stabilization and release kinetics.

Once loaded in the polysaccharide particles, the glassy matrix can protect delicate proteins from contact with organic solvents during microencapsulation processes. B-galactosidase, rhEPO and recombinant human granulocyte macrophage colony stimulating factor (rhGM-CSF) were loaded in AqueSpheres and washed with dichloromethane (DCM) and/or encapsulated in PLGA microspheres with DCM as the solvent. The bioactivity of these proteins can be well retained as determined with activity assay after the preparation treatments (Examples 5, 6, and 7). Contact with organic solvents is believed as the major chemical hazard in microencapsulation processes using degradable polymers (3).

In addition to resistance to organic solvents, AqueSpheres can protect proteins from aggregation and conformation change in a hydrated state at physiological temperature. Protecting delicate protein under such a condition is regarded as the most challenging technical hurdle in sustained protein release (21). We incubated hydrated-AqueSphres, loaded with rhGM-CSF and b-galactosidase respectively, at 37° C., and found that protein activity were well retained (Examples 8). For rhGM-CSF, there was no significant declining in bioactivity after incubation for 9 days (Example 8). For b-galactosidase, a comparison was made between AqueSphres and trehalose (a well recommended protein stabilizer (6) matrix under the same incubation condition. Proteins protected by AqueSpheres were 5 times active as that protected by trehalose after incubation for a week (Example 9).

AqueSpheres, when encapsulated in degradable polymer microspheres, offer an ideal release profile with extended linear kinetics and free of burst. PLGA microspheres are know to release loaded macromolecules in three phases (22): an initial burst due to rapid diffusion of the molecules located in the surface region (25) or internal water-filled pores (14) of the microspheres, a lag phase after the initial burst, and an accelerated release due to bulky degradation of the polymer. A burst effect, for which more than 50% loading may be released in the first day after administration, may be dangerous for many therapeutics. Due to the small and uniform size, particles prepared by this method dispersed evenly in the matrix of degradable polymers (Example 3) that there is no a surface-rich protein distribution. In addition, unlike small molecular weight protein stabilizers that readily dissolve (cause high osmotic pressure (11)) and rapidly diffuse out of the polymer matrix, AqueSpheres form a viscous phase that fills the diffusion channels when hydrated. Since the molecules of polysaccharide themselves diffuse gradually from the polymer matrix (23), protein burst can be suppressed (Example 9) by the viscous stabilizers. Moreover, the diffusion process may be extended so that it overlaps with the degradation process to give a single phase release kinetics (Example 9).

Interaction between proteins loaded and the degradable polymers is another problem that causes incomplete release and insoluble protein aggregation (18). In the present method, the protein molecules are surrounded by the viscous polysaccharides in side of a hydrated microsphere during the entire release period (23) so that the chance for protein-polymer contact is reduced. Release profiles of myoglobin encapsulated in PLGA microspheres directly and through AqueSpheres are compared in FIG. 10 (Example 9). For direct microencapsulation, less than 20% of the loaded proteins were release over 45 days. While for encapsulation through AqueSpheres, 70% of the loadings were released for the same period.

Local acidity in the PLGA matrix is another cause for protein denature (3). When the polymer degrades, the degradation products (lactic acid and glycolic acid as well as their oligomers) may be trapped inside of the polymer matrix and cause the local pH to decrease. In our system, AqueSpheres form an interconnected viscous phase when hydrated. These viscous channels, although less permeable to macromolecular proteins, are permeable to small molecular buffers so that the acidity degradation fragments may be buffered. In addition, alginate used as the surface modifier for the aqueous-aqueous emulsion (example 1) possesses a buffer effect. In a titration test, the pH was stabilized around 5 when 100 μl of 0.1 N HCl was added to 0.9 ml 150 mM (based on the monomer) alginate solution.

The present invention provides a simple yet effective solution by which all the technical challenges in sustained release protein delivery can be addressed. With this method, delicate proteins can be protected in steps of both formulation and administration, and release approximately constantly without a burst. The system demonstrated is expected to have a wide variety of applications for delivery of delicate therapeutics.

This invention provides polysaccharides (including their derivatives) capable of protecting delicate agents in microencapsulation. This polysaccharides include but are not limited to dextran, starch, cellulose and its derivatives, and agarose.

This invention provides the application of a polysaccharides particulate system which is prepared via a stable aqueous-aqueous emulsion as described in U.S. patent application Ser. No. 09/886,555 to deliver structurally delicate agent(s).

The structurally delicate agents include but not limit to proteins, peptides, DNA/RNA, liposomes, live viruses, oily microdroplets, and other bioactive agents; and proteins and peptides include but not limit to EPO, G-CSF, GM-CSF, interferon α and β, growth hormone, calcitonin, TPA, factor VIII, factor IX, and dornabe α.

This invention provides a method for preparing the polysaccharides particles (named as AqueSpheres in following) for encapsulation of structurally delicate agents.

a. providing a stable polymer aqueous-aqueous emulsion which is prepared under a condition free of chemical, physical or biological hazards such as organic solvent(s), crosslink agent(s), extreme pH, concentrated salt(s), strong shear stress, high interfacial tension and so forth;

b. selecting polysaccharides as the particulate (dispersed) phase for aqueous-aqueous emulsification from dextran, starch, cellulose, agarose and all type of poly- or oligo-sugars possess similar structure;

c. selecting aqueous polymers as the continuous phase from polyethylene glycol (PEG), polyethylene oxide (PEO), polyvinyl parrolidone (PVP), polyvinyl alcohol (PVA) and all other aqueous polymers whose aqueous solutions are immiscible with those of polysaccharides;

d. selecting stabilizing agent(s) and its (their) concentration for aqueous-aqueous emulsification (the agents include sodium alginate and other polymers of similar structure);

e. providing, at least one, agent(s) which include but not limited to proteins, peptides, DNA/RNA, liposomes, live viruses and oily microdroplets, and other bioactive agents being loaded in the dispersed phase;

f. selecting small sugars (e.g., trehalose, manitose, sucrose or golycerin) and concentration range as complimentary agents to polysaccharides for better protection of delicate agents encapsulated in AqueSpheres during successive steps;

g. controlling the size and shape of AqueSpheres into appropriate range for inhalation (1–5 μm), double microencapsulation (1–20 μm) and other applications (1–50 μm);

h. utilizing a drying process including freeze-dry (lyophilization), spray drying or a conventional drying process to solidified AqueSpheres; and i. removing the continuous phase after drying by washing the sample with solvent(s) which do not penetrate into the dried AqueSpheres, nor affect the loaded delicate agent(s).

This invention provides a method of encapsulating AqueSpheres into biodegradable polymer microspheres for controlled release of bioactive agent(s) comprising:

a. utilizing a solid-in-oil-in-water (S-O-W) emulsification process with AqueSpheres as the solid phase;

b. selecting the molecular weight (ranged 10,000–1,000,000) of polysaccharides(s) which forms AqueSpheres according to size of encapsulated delicate agents and required release rate;

c. selecting other excipients (includes but not limited to trehalose, manitose, gelatin and amino acids and their derivatives) used in the dextran phase for better protection of delicate agents;

d. selecting biodegradable polymers (PLGA, poly-pseudo serine and other polymers) to encapsulate AqueSpheres;

e. selecting polymeric surfactant(s) for dispersing AqueSpheres in the solution of biodegradable polymers;

f. selecting polymeric surfactant(s) for emulsifying the solution of the biodegradable polymers in water; and g. adding inorganic salt(s) in the water phase to improve loading efficiency of active agents.

This invention provides the method of using polysaccharide fine particles to pre-load ingredients so that control the release kinetics from sustained release polymer micrspheres including suppressing burst effect and preventing incomplete release.

This invention provides AqueSpheres in injectable implant systems for delivery of delicate therapeutics.

This invention provides the method of using AqueSpheres in injectable implant system comprising selecting an injectable solvent.

The invention will be better understood by reference to the Examples which follow, but those skilled in the art will readily appreciate that the specific examples are only illustrative and are not meant to limit the invention as described herein, which is defined by the claims which follow thereafter.

EXAMPLES

Example 1

Stability of Polymer Aqueous-Aqueous Emulsion

Stability of polymer aqueous-aqueous emulsion was examined by observation of the fusion (the size change) of the dispersed phase under a microscope and by observation of formation of block phases of the colored dispersed phase directly by eyes as a function of time. The dispersed phase contains dextran (MW=5,000~5,000,000; concentration=5~40 w/w %) and sodium alginate (MW: low, medium or high viscosity; concentration=0~5 w/w %). For colored experiment, 1~2 w/w % of blue dextran (MW=50,000~5,000,000) was added into the dispersed phase. The continuous phase contains PEG (MW=4,00~100,000; concentration=5~40 w/w %), sodium alginate (MW: low, medium or high viscosity; concentration=0~5 w/w %) and sodium chloride (concentration=0~5 w/w %).

Emulsions various contents of sodium chloride were prepared by adding the dextran solution to the PEG solution, followed by homogenizing with a mechanic homogenizer. Dextran to PEG ratio was 1:5 to 1:20. After the emulsions were prepared, a drop of the sample was subjected to a microscope for microscopic image taking. Then the samples were left in bottles for continuous observation.

FIG. 1 shows a picture of a polymer aqueous-aqueous emulsion after mixing was stopped and the emulsion stored at room temperature for a week. Myoglobin was used as a model protein that was loaded in the dispersed phase, showing the rusty color. Among the six samples, sample 4 was prepared without sodium alginate. Sample 6 was the same as samples 1 except that sodium chloride was added (to reach 100 mM). For these two samples, fusion of the dispersed phase occurred right after stirring was stopped, which led to formation of two block phases in a few hours. For the other four samples in FIG. 1, the droplet diameter remained in the range of 3–7 μm (FIG. 2A) during the week. This result supported our hypothesis that charged polymer molecules adsorbed at the droplet surface and created a diffuse double layer. Increasing the concentration of sodium ions, the counter ions of alginate, shelled the surface charge, reduced the magnitude of the zeta potential, and thus caused droplets to coalescence. Reducing the dextran/PEG ratio to 1:15 lead to an emulsion stable for two weeks.

In this experiment, the partition coefficient of myoglobin between the continuous phase and the dispersed phase was 1:50, as determined by absorbance at 410 nm, indicating that the majority of myoglobin was in the dextran phase. In addition to myoglobin, recombinant human granulocyte macrophage colony stimulating factor (rhGM-CSF) and liposomes carrying amphotericin B (AmB) were also loaded in the system and formed glassy particles similar to those in FIG. 2B. About 93% of rhGM-CSF and 95% of AmB/liposomes were partitioned in the dispersed phase as detected by activity assay (See later discussion) and UV absorbance at 408 nm, respectively.

FIG. 2A shows a microscopic image of a polymer aqueous-aqueous emulsion prepared with the sodium chloride free solutions described above. Emulsion droplets with a uniform size distribution between 3–8 microns in diameter were obtained.

Example 2

Preparation of AqueSpheres

AqueSpheres were prepared simply by freeze-drying the stable emulsions of above. After freeze-drying, the dextran droplets converted to solid particles. However, the most of dextran particles were dispersed in a solid matrix formed by the continuous phase, PEG. The PEG can be removed by washing the lyophilized powder with methylene chloride or acetonitrile. These solvents did neither dissolve nor swell the dried dextran phase. FIGS. 2A and 2B showed the microscopic images of the dispersed phase at different preparation stages: after emulsification, after freeze-drying followed by rinsing with dichloromethane (to remove PEG), and after recovery from PLGA coating, respectively. After freeze-drying, the diameter of the dispersed phase remained uniform but dropped from 3–7 μm to 1–3 μm, a reasonable size reduction from loss of water (See FIG. 2B). These images indicated that no droplet fusion occurred during lyophilization. This size range of the dried particles (1–3 μm) is ideal for inhalation delivery of therapeutics and is also suitable for preparation of degradable polymer coated microspheres via double encapsulation (S-O-W) (5, 13).

Example 3

Microencapsulation of AqueSpheres into PLGA Microspheres

AqueSpheres can be further microencapsulated into the matrix of PLGA and other biodegradable polymer microspheres through a "solid-in-oil-in-water" emulsification process. In the present study, PLGA with lactic:glycolic ratio of 50:50 and 75:25 were used. AqueSpheres prepared as in Example 2 were first suspended in a PLGA/dichloromethane solution (10–20%), then added into a water solution containing 0.1–10% sodium chloride and 0.5–5% polyvinyl alcohol (PVA) or PEG or polyvinyl parralidone (PVP) under stirring. The volume ratio of the two solutions was 1:5. After an emulsion was formed, the organic solvent was extracted by pouring the system into large volume of cold water (10 times of the emulsion) under stirring. FIGS. 3A and 3B show the microscopic images of the PLGA droplets before solvent extraction and PLGA particles after solvent extraction, respectively. Before solvent extraction, the PLGA droplets were transparent within which the encapsulated AqueSpheres were evenly distributed. After hardening by solvents removing, the PLGA particles lost transparency.

Example 4

Recovery of AqueSpheres from PLGA Particles

AqueSpheres can be recovered from the PLGA microspheres prepared as in Example 3. AqueSpheres loaded PLGA particles were re-dissolved in dichloromethane or acetonitrile, followed by centrifugation. This procedure was repeated several times until no polymer (PLGA) residues were observed under a microscope. FIG. 4 shows the AqueSpheres recovered from PLGA microspheres by the above mentioned procedure. The particle size and shape of AqueSpheres remain the same as before being encapsulated in PLGA microspheres. The result suggests that hydration of AqueSpheres during the microencapsulation process is not significant.

A weight measurement was carried out to examine encapsulation efficiency of AqueSpheres by the PLGA microspheres. A relatively constant weight ratio of dextran to PLGA was obtained before (1:19) and after (1.06:19) microencapsulation, suggesting high encapsulation efficiency. This conclusion consists with our result on protein activity assay before and after encapsulation (See Example 7).

Example 5

Protection of β-galactosidase by AqueSpheres Against Organic Solvents

To examine the effectiveness of AqueSpheres in protecting delicate proteins against organic solvents, β-galactosidase, an enzyme with quadral structure and molecular weight of 434 KD, was loaded into AqueSpheres. The protein was dissolved in a dextran solution and emulsified into a PEG solution as in Example 1. After freeze-dying, the PEG phase was removed by washing with dichloromethane (a popular solvent used in preparation of PLGA microspheres) several times as in Example 4. Then, the obtained protein-loaded AqueSpheres were re-dissolved in a buffer and assayed by hydrolysis of o-nitrophenyl-β-D-galactopyranoside (ONPG). As indicated in FIG. 5, the catalytic activity of the enzyme only decreased less than 10% after the procedure from Example 1 through Example 2 (included emulsification, freeze-drying and washing with dichloromethane). The result was reproducible by three runs. This 10% activity loss includes loss of the proteins by partition between the dextran and PEG phases in the emulsification process and by the washing process, as well as those denatured in freeze-drying and in the washing process and lost during the washing process. This result indicates that delicate proteins inside of AqueSperes can be well protected against organic solvents during microencapsulation process.

Example 6

Partition of rhEPO and rhGM-CSF in the Dispersed and the Continuous Phases of the Aqueous-Aqueous Emulsion A partition experiment was carried out to determine the efficiency of proteins being loaded in the dispersed phase of the emulsion system. The aqueous-aqueous emulsion containing recombinant human erythropoietin (rhEPO) or recombinant human granulocyte-macrophage colony stimulating factor (rhGM-CSF) was centrifuged, followed by a cell proliferation assay using a TF1 cell line. Protein activity was measured by counting the numbers of cells per well under a microscope. About 94% of rhEPO and 93% of rhGM-CSf were found in the dextran phase by the partition experiment.

Example 7

Protection of rhEPO and rhGM-CSF by AqueSpheres Against Organic Solvents

Protein-protection by AqueSpheres was further examined with the two proteins rhEPO and rhGM-CSF. The proteins were loaded in AqueSpheres and treated according the procedure identical to that in Example 5. Bioactivity of the proteins was assayed by the same cell proliferation method as for partition (Example 6). The proteins before encapsulation and recovered from AqueSpheres (after washing with dichloromethane) were added into same cell suspensions, respectively. The result for rhEPO is shown in FIG. 6. After freeze-drying, the activity retention for rhEPO was 85% as indicated by the drop of cell count from 27800 to 23700 per well. Washing the lyophilized powder (so the Peg phase was removed) resulted a further drop of the cell count to 22600, indicating that the activity retention was 95%. Because only 94% of proteins were remained in the dextran phase after washing with organic solvent (Example 6), the activity retention was 100% after contact with the organic solvent.

FIG. 7 shows the result of activity assay for rhGM-CSf after each preparation step. By freeze-drying the protein-loaded emulsion to a dry powder, the average number of cells per well reduced from 130900 to 122600, indicating roughly 94% of activity retention. After washing the freeze-dried powder with dichloromethane to remove residual PEG, the cell count decreased to 111100 per well, a 9% further reduction. Much of this 9% reduction, however, was caused by rhGM-CSF partitioned in the continuous phase (about 7% of total rhGM-CSF, Example 6) that was washed away along with PEG. Encapsulating the protein-loaded dextran particles into PLGA microspheres did not cause further activity decrease as indicated by an average cell count of 118900 per well. The high activity retention also indicated high encapsulation efficiency that was indicate by a weight measurement (Example 4).

Example 8

Activity Retention of rhEPO, rhGM-CSF and β-galactosidase by AqueSpheres in Hydrated State at Physiological Temperature It has been widely believed that the most challenging task in developing sustained release dosage forms of protein drugs is to ensure protein activity in a hydrated state at physiological temperature (18). During sustained release, the degradable polymer microspheres will absorb water and swell, and the encapsulated protein molecules will be exposed to a hydrated condition at body temperature. Hydration and temperature elevation will increase the mobility of protein molecules that increases the chance for chemical or physical changes of protein (19). To examine protein stability under physiological conditions, water was added to the dextran particles loaded with rhEPO or rhGM-CSF (to formed a viscous 30 w/w % dextran solution) and incubated at 37° C. Protein activity in FT1 cell proliferation was shown in FIGS. 8 and 9 as a function of incubation time.

For rhEPO, activity of those protected by AqueSpheres gradually declined to about 50% in a week (FIG. 8). For unprotected rhEPO, however, the same amount of activity declining took only one day. Half-life of rhEPO is 8.5 hrs in vivo due to enzymatic catalysis in the body. Clearly the viscous polysaccharide phase, formed by hydration of AqueSphere, can extend the protein activity at physiological condition for significant period of time.

Similar result was obtained for rhGM-CSF (FIG. 9). For protected rhGM-CSF, activity retention was 85% after 10 days of incubation. That of unprotected rhGM-CSF was 56% for the same incubation period.

The protection effect of polysaccharide stabilizers for b-galactosidase in hydrated state was compared with that of trehalose. The activity assessment was carried out same as in Example 5. After 7 days of incubaion at 37° C., the activity for the protein stabilized by polysaccharide declined to 89% while that stabilized by trehalose declined to 17%.

Example 9

Protein Release Profile with Mimimal Burst and Incomplete Release from PLGA Microspheres Burst effect and incomplete release are another common problem in development of sustained release dosage form of protein drugs. Due to burst effect, 30–70% of proteins loaded maybe release immediately after administration. Incomplete release referes to that 20–40% of the loadings remained as insoluble residues. This undesired release can be prevented by pre-loading proteins in AqueSphere. The protein was loaded into AqueSpheres (0.1–20%) through the aqueous-aqueous emulsification process first. Then the protein-loaded AqueSpheres were encapsulated in PLGA microspheres (1–20%) using a S-O-W technique. Loading capacity of myoglobin in PLGA was 0.25 to 5%. PVA, PEG and PVP were dissolved in the water phase (0.1–5%) as surfactants. FIG. 10 shows release profiles of myoglobin encapsulated to PLGA (with the end group blocked) microspheres with and without protection of AqueSpheres. When myoglobin was encapsulated as pure protein particles into microspheres made of ester-end PLGA, only 17% of the loaded protein was released over 45 days. For myoglobins encapsulated after pre-loaded in AqueSpheres, up to 75% of the loaded protein was released linearly over 45 days without a burst release in the beginning. Such a burst-free linear release was also achieved when the myoglobin-dextran particles were encapsulated in microspheres of a relatively hydrophilic acid-ended PLGA (FIG. 11).

FIG. 11. shows the myoglobin release profiles from microspheres made of acid-end PLGA (molecular weight=12K) with lactide:glycolide ratio of 50:50, 65:35 and 75:25, respectively. For all these samples, myoglobin were pre-formulated to AqueSpheres prior to encapsulation into PLGA microspheres. About 7 to 12% loadings were released in the first day, followed by a linear kinetics. From microspheres made of PLGA with L/G of 50/50 and 65/35 and MW of 12K, protein release was over 90% in 50 days, almost complete. Increase in the L/G ratio from 65/35 to 75/25 resulted in slightly a decreased release rate as that 80% of loadings was released in the same time period. Release rate also declined by increase of molecular weight (MW) from 12K to 20K. For the PLGA with L/G ratio of 65/35, 65% of myoglobin encapsulated was released during 50 days. In either of the cases, the release profile were almost linear. Encapsulation efficiency of myoglobin into PLGA microspheres by this methods was about 90% based on analysis of the protein content in the supernatant of after the preparation process.

REFERENCES

1. R. Langer, Folkman, J., Nature 263, 793–800 (1976).
2. CAS, "Search on Chemical Abstracts resulted in 962 research articles and patents on the subject of sustauned release of proteins based on degradable polymers." (2002).
3. M. V. Weert, Hennink, W. E., Jiskoot, W., Pharm. Res. 17, 11591167 (2000).
4. R. T. Bartus, Tracy, M. A., Emerich, D. F., Zale, S. E., Science 281, 1161–1162 (1998).
5. P. A. Burke, Handbook of pharmaceutical controlled release technology Marcel Dekker, 661–692 (2000).
6. J. L. Cleland, Jones J. S., Pharm. Res. 13, 1464–1475 (1996).
7. O. L. Johson, Pharmaceutical Research 14, 730–735 (1997).
8. B. C. Cunningham, Mulkerrin, M. G., Wells, J. A., Science 253, 545–548 (1991).
9. S. E. Zale, Burke, P. A., Berstein, H., Brickner, A., in U.S. Pat. No. 5,716,644. (USA, 1998).
10. A. Sanchez, Villamayor, B., Guo, Y., Mclver, J., Alonso, M. J., Intern. J. Pharm. 185, 255–266 (1999).
11. S. P. Schwendeman, Tobio, M., Jaworowicz, M., Alonso, M. J., Langer, R., J. Microencapsulation 15, 299–318 (1998).

12. M. Morlock, Koll, H., Winter, G., Kissel, T., European Journal of pharmaceutics and biopharmaceutics 43, 29–36 (1997).
13. S. Yoshioka, Aso, Y., Kojima, S., Pharmaceutical Research 14, 736–741 (1997).
14. M. v. d. Weert2, Hof, R. V., Weerd, J. v. d., Heeren, M. A., Posthuma, G., Hennink, W. E., Crommelin D. J. A., J. Controlled Release 68, 31–40 (2000).
15. T. Morita, Horikiri, Y., Suzuki, T., Yoshino, H., International Journal of Pharmaceutics 219, 127–137 (2001).
16. Y.-F. Maa, Nguyen, P-A., Hsu, S. W., J. Pharm. Sci., 87, 152–159 (1997).
17. T. Morita, Horikiri, Y., Yamahara, H., Suzuki, T., Yoshino, H., Pharm. Res. 17, 1367–1373 (2000).
18. T. G. Park, Lee, H. Y., Nam, Y. S., J. Controlled Release 55, 181–191 (1998).
19. O. Franssen, W. E. Hennink, Intern. J. Pharm., 168, 1–7 (1998).
20. F. Lamberti, in WO96/40071 (1996).;
21. S. P. Schwendeman, Cardamone, M., Brandon, M. R., Klibanov, A., Langer, R., Stability of proteins and their delivery from biodegradable polymer microspheres. S. C. H. Bernstein, Ed., Microparticulate Systems for the Delivery of Proteins and Vaccines (Mercel Dekker, New York, 1996), vol. 77.
22. W. R. Liu, Langer, R., Klibanov, A. M., Biotech. Bioeng. 37, 177–184 (1991).
23. B. Bittner, Morlock, M., Koll, H., Winter, G., Kissel, T., Eur. J. Pharm. Biopharm. 45, 295–305 (1998).
24. T. Jin, L. Chen, H. Zhu, U.S. patent application Ser. No. 09/886,555 (2001).
25. H. Takahata, Lavelle, E. C., Coombes, A. G. A., Davis, S. S., J. Controlled Release 50, 237–246 (1998).

What is claimed is:

1. A composition for microencapsulation comprising glassy particles with diameters below 10 μm made of a polysaccharide with similar structure to dextran for protecting biological agents in microencapsulation without ionic or covalent cross-linking agents.

2. The composition of claim 1, further comprising an outer layer of biodegradable polymer.

3. The composition of claim 1, wherein the polysaccharide is selected from the group consisting of dextran, starch, cellulose, carboxymethylcellulose, alginate, and agarose.

4. The composition of claim 1, further comprising a biological agent selected from the group consisting of proteins, peptides, DNA, RNA, and live viruses which can be loaded in a polysaccharide with similar structure to dextran by preferential partition.

5. The composition of claim 1, further comprising a biological agent selected from the group consisting of erythropoietin, granulocyte colony stimulating factor, granulocyte-macrophage colony stimulating factor, interferon α and β, growth hormone, calcitonin, factor VIII, and factor IX.

6. A method for encapsulating biological agents into particles comprising:
    a. selecting an appropriate polysaccharide with similar structure to dextran, as the dispersed phase for aqueous-aqueous emulsification, selecting an aqueous polymer of appropriate size, selected from the group consisting of polyethylene glycol (PEG), polyethylene oxide (PEO), polyvinyl pyrrolidone (PVP), and polyvinyl alcohol (PVA), as the continuous phase, and selecting appropriate stabilizing agent(s) for aqueous-aqueous emulsification, to provide a stable polymer aqueous-aqueous emulsion which is prepared under a condition without ionic or covalent cross-linking agents;
    b. providing, at least one, biological agent;
    c. controlling the size and shape of said biological agent to an appropriate range;
    d. drying the emulsion; and
    e. removing the continuous phase by washing with solvent(s) that dissolves said aqueous polymer.

7. The method of claim 6, performed under a condition free of chemical or physical hazards.

8. The method of claim 7, wherein the chemical or physical hazard is selected from the group consisting of organic solvent, crosslinking agent, pH below 2 or above 8, strong shear stress, and high interfacial tension.

9. The method of claim 6, further comprising selecting small molecular sugars, selected from the group consisting of trehalose, manitose, sucrose, and glycerin, and concentration ranges from 0.1% to 8% as complementary agents to a polysaccharide with similar structure to dextran for better protection of biological agents encapsulated in the polysaccharide particles during successive steps.

10. The method of claim 6, wherein, a polysaccharide with similar structure to dextran is selected from the group consisting of dextran, starch, cellulose, carboxymethylcellulose, alginate, and agarose.

11. The method of claim 6, wherein the stabilizing agent is a polysaccharide possessing a negatively charged backbone and positively charged counter ions, selected from the group consisting of sodium alginate, carboxyl cellulose, and dextran sulphate.

12. The method of claim 6 or 11, wherein the concentration of the stabilizing agent is below 10%.

13. The method of claim 6, wherein the biological agent is selected from the group consisting of proteins, peptides, DNA, RNA, and live viruses.

14. The composition of claim 1, wherein the diameter of the glassy particles is 1–5 μm for inhalation, and 0.5–10 μm for further microencapsulation.

15. The method of claim 6, wherein drying of the emulsion is selected from the group consisting of lyophilization, spray drying, and conventional drying process to solidify encapsulated polysaccharide with similar structure to dextran.

16. The method of encapsulating AgueSpheres into biodegradable polymer microspheres for controlled release of biological agent(s) comprising:
    a) utilizing a solid-in-oil-in-water (S-O-W) emulsification process with AqueSpheres as the solid phase;
    b) selecting the molecular weight of a polysaccharide for forming AqueSpheres according to size of encapsulated biological agents and required release rate;
    c) selecting excipients used in the dextran phase for better protection of biological agents;
    d) selecting biodegradable polymers to encapsulate AqueSpheres;
    e) selecting polymeric surfactant(s) for dispersing AqueSpheres in the solution of biodegradable polymers;
    f) selecting polymeric surfactant(s) for emulsifying the solution of the biodegradable polymers in water;
    g) adding inorganic salt(s) in the water phase to improve loading efficiency of biological agents;
    h) adding an AqueSpheres-suspended polymer solution into an aqueous buffer, followed by emulsification;
    i) Solidifying the droplets and drying the solidified particles.

17. The method of claim 16, wherein the molecular weight of the polysaccharide is about 10,000–1,000,000.

18. The method of claim 16, wherein the excipient is selected from the group consisting of trehalose, manitose, sucrose, and amino acids.

19. The method of claim 16, wherein the biodegradable polymers are selected from the group consisting of poly-lactic glycolic acid, poly-pseudo serine, and polyanhydrides.

* * * * *